United States Patent [19]

Andersen

[11] Patent Number: 5,058,599
[45] Date of Patent: Oct. 22, 1991

[54] METHOD AND APPARATUS FOR DETECTING A SEQUENCE OF ABNORMAL EVENTS IN AN ELECTRICAL SIGNAL, PARTICULARLY IN THE DEPOLARIZATION SIGNAL OF A HEART

[75] Inventor: Hans Andersen, Voellingby, Sweden

[73] Assignee: Siemens Aktiengesellschaft, Munich, Fed. Rep. of Germany

[21] Appl. No.: 538,107

[22] Filed: Jun. 14, 1990

[30] Foreign Application Priority Data

Jun. 15, 1989 [EP] European Pat. Off. ........ 89110885.4

[51] Int. Cl.⁵ .............................................. A61B 5/04
[52] U.S. Cl. .................................... 128/705; 128/703
[58] Field of Search ................................ 128/702–705, 128/419 D

[56] References Cited

U.S. PATENT DOCUMENTS

| | | | |
|---|---|---|---|
| 3,612,041 | 10/1971 | Ragsdale | 128/705 |
| 3,703,900 | 11/1972 | Holznagel | 128/419 |
| 3,861,387 | 1/1975 | Lawhorn et al. | 128/2.06 |
| 3,978,856 | 9/1976 | Michel | 128/703 |
| 4,184,493 | 1/1980 | Langer et al. | 128/419 |
| 4,202,340 | 5/1980 | Langer et al. | 128/419 |
| 4,342,318 | 8/1982 | Engle et al. | 128/708 |
| 4,393,877 | 7/1983 | Imran et al. | 128/419 D |
| 4,523,595 | 6/1985 | Zibell | 128/419 D |
| 4,905,708 | 3/1990 | Davies | 128/705 |

Primary Examiner—William E. Kamm
Attorney, Agent, or Firm—Hill, Van Santen, Steadman & Simpson

[57] ABSTRACT

A method and apparatus for detecting a sequence of abnormal events in an electrical signal, such as the depolarization signal of the heart, compares a selective signal parameter to a defined threshold, and measures the maximum value of the signal parameter for each event which exceeds the threshold. The characteristic quantity corresponding to the statistical distribution of the respective maximum values for a defined number of most recently, successively occurring events is calculated, with each newly measured maximum value causing the characteristic quality to be updated. The characteristic quality is compared in a comparator to a defined rated value, and a signal indicating the presence of a sequence of abnormal events in the electrical signal is generated if the characteristic quality differs from the rated value by more than a selected amount.

12 Claims, 5 Drawing Sheets

METHOD AND APPARATUS FOR DETECTING A SEQUENCE OF ABNORMAL EVENTS IN AN ELECTRICAL SIGNAL, PARTICULARLY IN THE DEPOLARIZATION SIGNAL OF A HEART

BACKGROUND OF THE INVENTION

1. Field of the Invention

The present invention is directed to a method and apparatus for detecting a sequence of abnormal events among a plurality of normal events in an electrical signal. The method and apparatus are particularly suited for detecting a sequence of events indicating fibrillation among a plurality of normal events in the depolarization signal of a heart, wherein the fibrillation is detected and a defibrillation therapy is automatically administered.

2. Description of the Prior Art

The detection of a sequence of abnormal events among a plurality of normal events in an electrical signal is necessary for detecting arrhythmias in the depolarization signal of a pathological heart. In addition to waveforms indicating normal heart activity, the depolarization signal of a pathological heart contains waveforms which occur given the appearance of an arrhythmia, for example fibrillation, which deviate from the waveforms which are present in the case of normal heart activity. If the waveforms corresponding to a normal heartbeat are considered to represent a normal event in the heart depolarization signal, and the waveforms corresponding to an abnormal heartbeat are considered to represent an abnormal event in the depolarization signal, an arrhythmia represents a sequence of abnormal events among a plurality of normal events in the signal. Since a heart arrhythmia may present a life threatening situation, it is desirable to be able to quickly and reliably detect a sequence of events indicating an arrhythmia among a plurality of normal events in the heart depolarization signal to permit initiation of therapeutic measures sufficiently rapidly. Particularly for automatic defibrillators, it is necessary to accurately and reliably detect a sequence of events indicating fibrillation of the heart among a plurality of normal events. Only by doing so is it assured that first, the heart receives the defibrillation pulses required for terminating the fibrillation and second, that unnecessary defibrillation pulses, which can endanger the patient, are avoided.

A device for detecting heart rhythm irregularities, is described in U.S. Pat. No. 3,861,387. In this device, a signal corresponding to the electrical activity of the heart is acquired and the first time derivate of this signal is formed. The peak amplitude of the signal is calculated for each normal or abnormal event in the differentiated signal, and the mean value is continuously formed for a defined plurality of the most recently measured peak amplitudes. Proceeding from this continuously calculated mean value, a threshold is defined and the duration for which the amplitude is above the threshold over the duration of the event is calculated for each event in the differentiated signal. The mean value of a defined plurality of most recently measured time durations is also continuously formed. The peak amplitude, as well as the chronological duration for which the amplitude was above the threshold, are compared to the respective mean values for each event which has occurred in the differentiated signal. As soon as one event exhibits a difference, exceeding a defined limit, form at least one mean value, a signal is generated which indicates the presence of an abnormal event. The decision as to whether an abnormal or a normal event is present is thus not based on objective criteria. To the contrary, it ensues with reference to criteria, namely, mean values, which are defined from the signal being investigated. This may, nonetheless, lead to unusable results in the detection of abnormal events, because events which are detected as abnormal are not taken into consideration in the formation of the mean values. The detection of sequences of abnormal events requires that the generation of signal indicating one abnormal event be suppressed until a defined plurality of abnormal events has been detected within a selected time interval. This is not possible with adequate reliability in the system described in U.S. Pat. No. 3,861,387. This is because if a signal initially contains only objectively normal events and the number of abnormal events occurring within the signal changes only gradually, these events will not be detected because a gradual change of the mean values occurs in gradual change of the signal, and eventually objectively abnormal events will come to be erroneously considered as normal events.

SUMMARY OF THE INVENTION

It is an object of the present invention to provide a method and apparatus for detecting a sequence of abnormal events in an electrical signal, particularly in the depolarization signal of a heart, such that the detection of a sequence of abnormal events in the signal is insured with high reliability under all circumstances, particularly given the occurrence of gradual changes in the events.

A further object of the present invention is provide a method and apparatus for detecting a sequence of events in the depolarization signal of a heart which indicates fibrillation, and to take automatic steps to administer defibrillation therapy to the heart, with high reliability and efficiently.

In the method disclosed herein, a signal parameter which is typical for the events to be detected is determined. A characteristic quantity corresponding to the statistical distribution of the maximum values of this selected signal parameter is calculated. The selected signal parameter may, for example, be the amplitude of the signal, the slope of the signal, the frequency of the signal, or another signal feature. The characteristic statistical quantity is compared to a rated value for that statistical quantity to determine whether the events taken into consideration in the formation of the statistical quantity contain a sequence of abnormal events, or are themselves parts of a sequence of abnormal events. The detection of a sequence of abnormal events thus ensues with reference to an objective criterion, because the rated value of the characteristic quantity (standard deviation) is no way dependent on the curve of the signal.

The maximum value of the selected signal parameter is also measured for each event, and each maximum value is compared to a defined threshold. This defined threshold will be exceeded by the signal in case of a normal event as well as in the case of an abnormal event. By suitable selection of the threshold disturbances which may be erroneously considered to be an event are not taken into consideration in the calculation of the standard deviation of the maximum values. The method of the invention thus permits a sequence of abnormal values to be detected with high reliability among a plurality of normal events in an electrical signal. The reliability of the detection increases with the number of events which are used for the calculation of the standard deviation. It is clear that in the method disclosed herein the time is lengthened from the appearance of a sequence of abnormal events to that time at which the comparison of the calculated characteristic quantity (standard deviation) to the rated value indicates the presence of a sequence of abnormal events. A compromise between the time permitted for the detection and the number of events to be used for the calculation of the characteristic quantity must be made. The method is therefore less suitable for detecting individual abnormal events among a plurality of normal events.

Any appropriate statistical quantity may be used as the characteristic quantity corresponding to the statistical distribution of the measured maximum values. The arithmetic mean value may be used, however in a preferred embodiment the standard deviation is used as the characteristic quantity. Even when the measured maximum values of the events are scattered within certain limits, use of the standard deviation still permits a precise decision to be made as to whether a sequence of abnormal events is present.

The standard deviation is usually identified by the character S. Calculation of this statistical quantity is well-known and is described, for example in the text Praktikum der Physik, Walcher (3rd edition, 1974) pp. 24ff. Many analog and digital circuits for calculating the standard deviation are known in the art.

In one embodiment of the invention, the difference between the maximum value and the threshold of the signal parameter is calculated for each event, and forms the basis for calculating the characteristic statistical quantity. The standard deviation is thus calculated with reference to what is referred to as a detection margin which, if desired, can also be expressed as a fraction or a percentage of the threshold. This is particularly useful since the relation of the maximum values to the threshold can thus be immediately recognized.

As noted above, the method disclosed herein is particularly suitable for detecting a sequence of abnormal events in the depolarization of a pathological heart. Given the selection of a suitable signal parameter for comparing the depolarization signal to the threshold and for which the maximum value of each that is measured, and given a suitably selected threshold, by calculating the characteristic quantity and defining a suitable rated value for the characteristic quantity, the appearance of malfunctions such as arrhythmias can be reliably detected.

An apparatus is also disclosed herein operating in accordance with the method described above. The apparatus has a simple structure, because the means for measuring the maximum value and the means for calculating the characteristic quantity corresponding to the statistical distribution of the measured maximum values need be present for only a single signal parameter. In a preferred embodiment of the invention, the means for calculating a characteristic quantity corresponding to the statistical distribution of the measured maximum values calculates the standard deviation. If, for achieving objectivity with respect to the individual events, the maximum values are to be indicated as a detection margin in relationship to the threshold, means for calculating the difference between the maximum value for an event and the threshold of the signal parameter are provided. The means for calculating the characteristic statistical quantity is supplied with the difference, so calculated, for the individual events. As with the method, the apparatus disclosed herein is particularly suited for detecting a sequence of abnormal events in the depolarization signal of a pathological heart.

As also noted above, the method and apparatus are particularly suited for detecting fibrillation. For this purpose, a signal parameter to be examined must be defined. For this embodiment, the signal parameter used is the chronological duration for which the amplitude of the signal, beginning at a time when the slope of the depolarization signal reaches a defined value, corresponds at least to the product of a defined slope and an elapsed time. The threshold is thus formed by a minimum chronological duration for which the depolarization signal exceeds that product, both given the appearance of a normal event and the appearance of an event indicating fibrillation. The maximum value which is measured is the overall chronological duration for which the amplitude of the depolarization signal, during an event, at least corresponds to the product of defined slope and elapsed time. The standard deviation of the overall chronological duration, or the detection margin, is calculated as the characteristic statistical quantity.

It has been found that the depolarization signal of the heart given normal heartbeats (sinus rhythm) has roughly the same overall chronological duration for each event. This means that each repetitive waveform in the sinus rhythm will have substantially the same overall chronological duration for which the amplitude of the depolarization signal at least corresponds to the product of the defined slope and elapsed time. The standard deviation of the overall chronological durations, measured for the most recently occurring event and for a defined plurality of continuously appearing events preceding the most recently measured even, is correspondingly low. If the heart no longer follows the sinus rhythm, which is the case given fibrillation, the overall chronological durations measured for the individual events fluctuate considerably, which is reflected in an increase in the standard deviation of the overall chronological durations. A reliable detection of a sequence of abnormal events, which are based on a rhythm differing from the sinus rhythm is thus possible with the method and apparatus of the invention. Thus a sequence of abnormal events indicating fibrillation of the heart can be detected.

The method and apparatus thus take into account not only the standard deviation of the overall chronological duration measured in conjunction with a defined number of most recently occurring events, but also take into account the heartbeat frequency (occurrence rate) which will be above a defined limit given the appearance of fibrillation. A reliable fibrillation detection is thus guaranteed.

In a further embodiment of the invention, the apparatus can be provided with means for administering automatic defibrillation therapy to the heart when the presence of defibrillation is detected. The fibrillation therapy is in the form of a defibrillation pulse, and given the presence of a signal indicating fibrillation, the heart is charged with at least one defibrillation pulse. Because the signal indicating fibrillation will be generated only when the above two conditions are met, the risk that the heart will be charged with a defibrillation pulses in the absence of actual fibrillation is extremely low.

DESCRIPTION OF THE PREFERRED EMBODIMENTS

Figure 1:
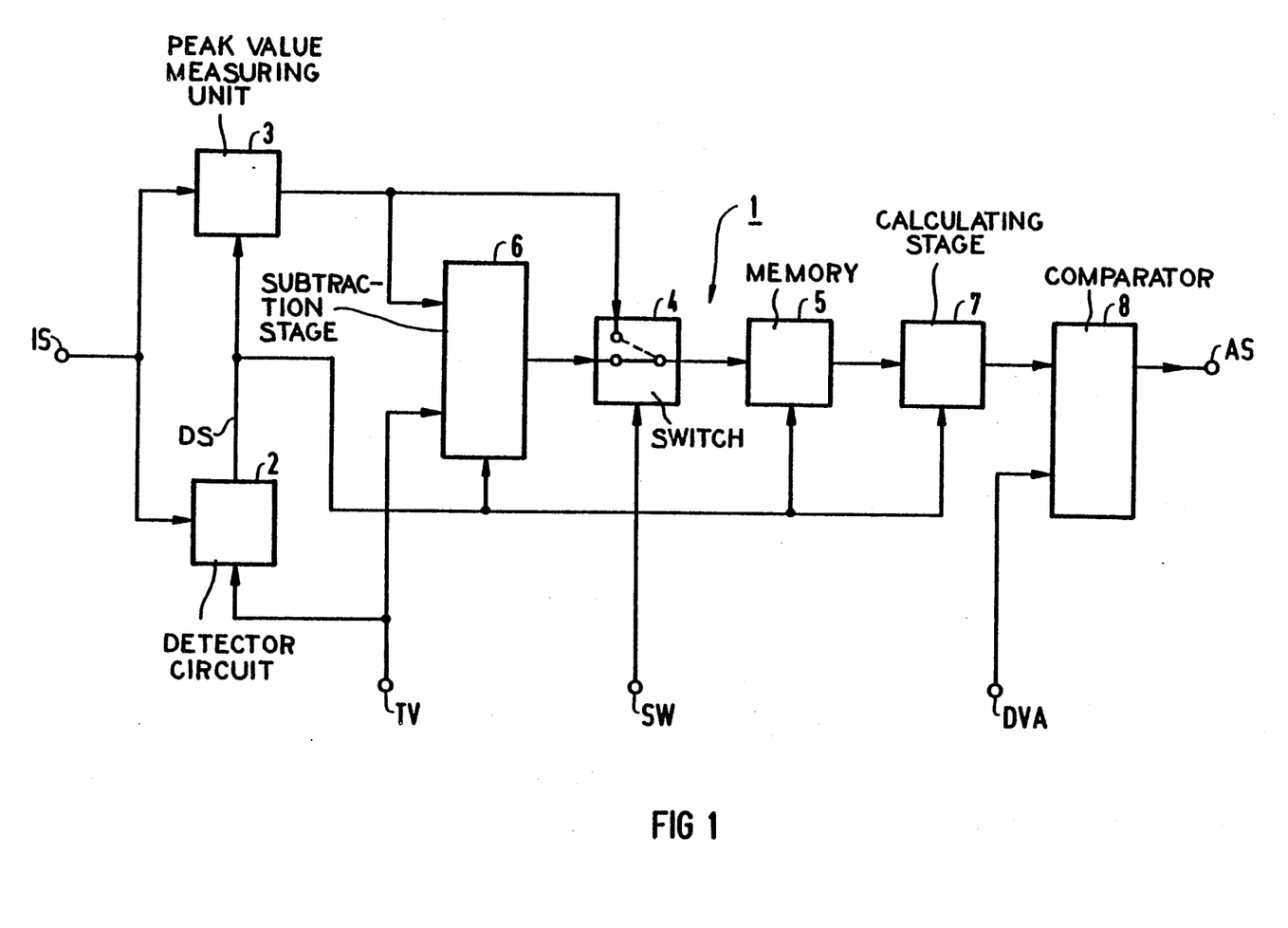
FIG. 1 is a schematic block diagram of an apparatus for detecting a sequence of abnormal events among a plurality of normal events in an electrical signal, constructed in accordance with the principles of the present invention.

An apparatus 1 is shown in FIG. 1 constructed and operating in accordance with the principles of the present invention which serves the general purpose of detecting a sequence of abnormal events among a plurality of normal events in an electrical signal IS. As shown in FIG. 1, the input signal IS proceeds to a detector circuit 2 which compares a signal parameter (for example, amplitude and/or slope) of the signal IS to a defined threshold. The defined threshold is supplied as a signal TV to the detector circuit 2 from ta source not specifically shown in FIG. 1. The signal parameter of the signal IS which is detected, or compared, in the detector circuit 2 will exceed the threshold given the appearance of a normal event as well as given the appearance of an abnormal event. By varying the signal TV, the threshold is programmable. The detector circuit 2, however, may be constructed with a fixed threshold. Each time an event occurs which exceeds the defined threshold with respect to the signal parameter, the detector circuit 2 generates a detector signal DS as an output.

The signal IS also proceeds to a peak value measuring unit 3, which responds to the same signal parameter as the detector circuit 2. When enabled by the detection signal DS, which is supplied to a control input of the peak value measuring unit 3, the peak value measuring unit 3 measures the maximum value of the signal parameter for each event i.e., for each enablement by the detection signal DS.

The output of the peak measuring value unit 3 is supplied to a switch 4. If the switch 4 is in the position indicated by the dashed line, the output of the peak measuring value unit 3 will be entered in a memory 5, also enabled by the detection signal DS. A memory 5 stores a selected number peak values for the respectively most recently occurring events. When a new maximum value is entered into the memory 5, the "oldest" event stored therein is erased.

A signal SW causes the switch 4 to assume the position indicated by the solid line, so that the input of the memory 5 is connected to the output of a subtraction stage 6, also controlled by the detection signal DS. The subtraction stage 6 forms the difference, for each event, between the peak value for that event, as measured by the measuring unit 3, and the aforementioned threshold for the signal parameter. For this purpose, the subtraction stage 6 is also supplied with the signal TV which sets the threshold. Dependent on the position of the switch 4, either the maximum values of the signal parameter, or the differences between the maximum values and the threshold, are stored in the memory 5 for the most recently occurring event and for a defined number of events immediately preceding the most recently occurring event. The differences correspond to detection margins for the respective events.

Upon the occurrence of each new event, the maximum values, or the differences, stored in the memory 5 are supplied to a calculating stage 7, which calculates a characteristic quantity corresponding to the statistical distribution of the measured maximum values, or to the statistical distribution of the calculated differences. This characteristic quantity may, for example, be the arithmetic mean value or the standard deviation. In each case, therefore, the calculating stage 7 calculates such a characteristical quantity. This calculated characteristic statistical quantity may be calculated on the basis of the measured maximum values themselves, or on the basis of the differences (detection margins) of these values from the threshold.

A signal corresponding to the calculated statistical characteristic quantity is supplied to a comparator 8, wherein this signal is compared to a value DVA supplied to another input of the comparator 8. The signal DVA corresponds to a rated value of the characteristics statistical quantity. The rated value, i.e., the magnitude of the signal DVA, is selected so that no output signal will be generated by the comparator 8 if the electrical signal IS essentially contains only normal events. If the signal IS contains a sequence of abnormal events, contains only abnormal events, this will result in a departure of the characteristic statistical quantity from the rated value DVA, in which case an output signal AS will be generated by the comparator.

As required, the comparator 8 may be constructed to generate an output signal AS when the signal corresponding to the calculated characteristic statistical quantity exceeds the rated value, falls below the rated value, or departs from a "window" of rated values.

Figure 2:
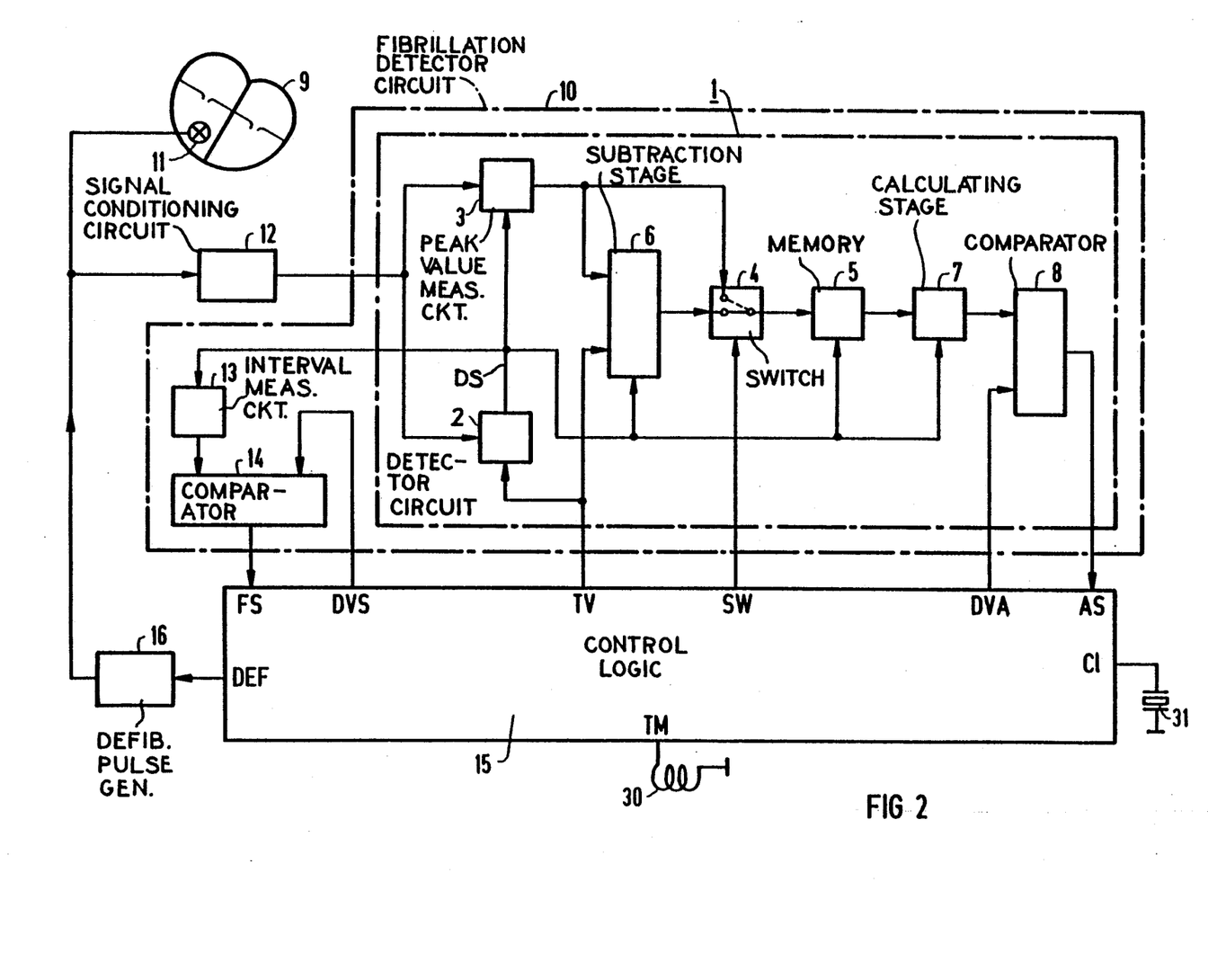
FIG. 2 is a schematic block diagram of an apparatus for detecting fibrillation in a heart and for automatically administering defibrillation therapy constructed in accordance with the principles of the present invention.

The embodiment of the apparatus of FIG. 1 in an apparatus for automatically detecting and treating fibrillation of a pathological heart 9 is shown in FIG. 2. The apparatus may be implanted in the body of a patient, similar to a heart pacemaker, by being miniaturized and contained within a suitable housing. The apparatus will terminate a condition of the heart known as fibrillation by supplying one or more fibrillation pulses, as needed. In order for the apparatus to operate automatically, it must first reliably detect the appearance of fibrillation. For this purpose, the apparatus of FIG. 2 includes a fibrillation detector circuit 10 which is supplied with the depolarization signal of the heart 9. The depolarization signal is obtained via an electrode 11 implanted, for example, in a ventricle of the heart 9, and is supplied to a signal conditioning circuit 12 wherein it is amplified and, if necessary, filtered before proceeding to the fibrillation detector circuit 10. The fibrillation detector circuit 10 contains the circuit 1 of FIG. 1. When used in the embodiment of FIG. 2, the apparatus of FIG. 1 serves to detect a sequence of abnormal events in the depolarization signal of the heart 9 which indicates the presence of fibrillation. The details of how the circuit 1 functions for that purpose are described below. For the moment, it is only necessary to state that the memory 5 has a capacity which is sufficient for storing the maximum values, or the data corresponding thereto, for at least twenty, and typically fifty, most recently occurring event. The calculating circuit 7 preferably calculates the standard deviation as the characteristic statistical quantity, and the standard deviation is compared in the comparator 8 to a rated value in the form of the signal DVA.

The fibrillation detector circuit 10 also contains a measuring circuit 13, which is enabled by the detection signals DS, and which measures the time interval between successive detector signals DS, i.e., a quantity corresponding to the heartbeat frequency (occurrence rate). The output signal of the measurement circuit 13 proceeds to a comparator 14, wherein it is compared with a signal DVS corresponding to a defined heartbeat frequency. If the output of the measurement circuit 13 exceeds the signal DVS, fibrillation may possibly be present. If the value DVS is exceeded by the output of the measurement circuit 13, the comparator 14 supplies an output signal FS to control logic 15 connected to the fibrillation detector circuit 10. If the comparator 8 generates an output signal AS, this is also supplied to the control logic 15.

If the control logic 15 simultaneously receives signals AS and FS from the respective comparators 8 and 14, control logic 15 actuates a defibrillation pulse generator 16 with a signal DEF. This causes the generator 16 to generate one or more defibrillation pulses, which are supplied to the heart 9 via the same electrode 11 which also serves for the acquisition of the depolarization signal. It is clear, however, that a separate electrode may be used for charging the heart 9 with defibrillation pulses.

As shown in FIG. 2, the defibrillating detector circuit 10 is supplied with the signals TV, DVA, DVS and SW by the control logic 15, the purpose of these signals having been already described.

Figure 3:
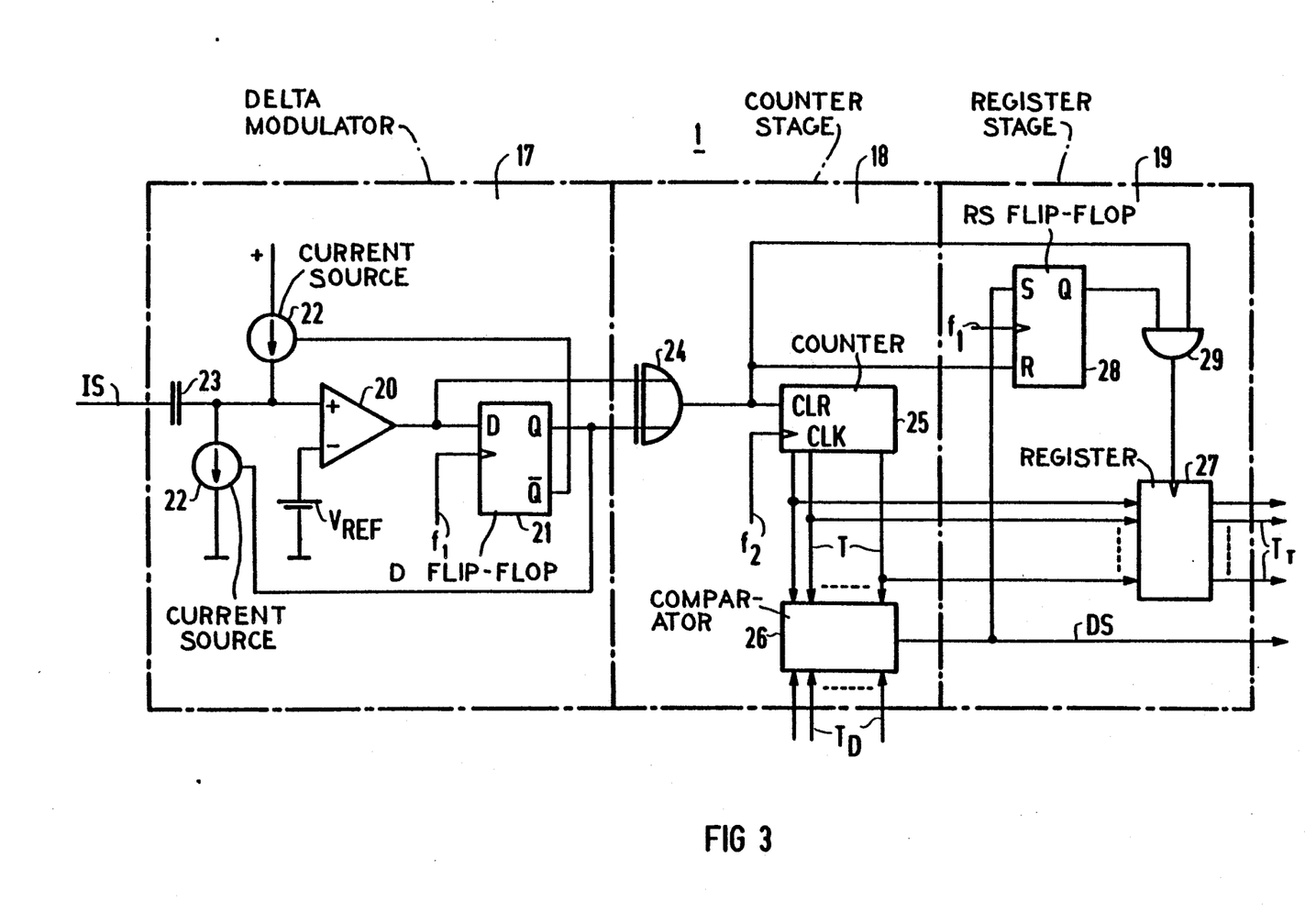
FIG. 3 is a circuit diagram or portions of the apparatus shown in FIG. 2.

A detailed circuit diagram is shown in FIG. 3 which executes the function of the detector circuit 2 and the peak value measuring unit 3 of FIGS. 1 and 2. The circuit of FIG. 3 is a digital circuit, which is preferable in view of the collaboration with the control logic 15. It will be understood, however, that the circuit of FIG. 3 can be easily realized as an analog circuit, if desired. The circuit of FIG. 3 comprises a delta modulator 17, a counter stage 18 and a register stage 19.

The delta modulator 17 includes a comparator 20, a D-flipflop 21, current sources 22, and an integration capacitor 23. The inverting input of the comparator 20 is connected to a reference voltage $V_{REF}$. The D-flipflop 21 is clocked with a frequency $f_1$ of, for example, 16 kHz.

The counter stage 18 includes an exclusive OR gate 24, a counter 25 clocked with the frequency $f_2$ of, for example, 8 kHz, and a comparator 26. The comparator 26 compares the output value T of the counter 25 to the rated value $T_D$, which corresponds to a defined chronological duration $t_D$. If the output value of the counter 25 exceeds the threshold $T_D$, a detection signal DS is generated.

The register stage 19 contains a register 27 which is clocked via a RS-flipflop 28 and via an AND gate 29, the RS-flipflop 28 is clocked with the frequency $f_1$. The register 27 stores the maximum output value of the counter 25 which the counter 25 reaches following the generation of a detection signal DS.

As long as the slope of the depolarization signal IS supplied to the circuit of FIG. 3 does not exceed the value $+1/C$ or falls below the value $-1/C$, (wherein $+1$ and $-1$ correspond to the current flowing through the current sources 22, the current being capable of being varied, and wherein C is the capacitance of the integration capacitor 23), the D-flipflop 21 continually switches. This causes the counter 25 in the counter stage 18 to be continuously reset to zero via the exclusive OR gate 24. If the slope of the depolarization signal IS exceeds 30 $1/C$ or falls below $-1/C$, the output of the comparator 20 retains its state for as long as the amplitude of the depolarization signal IS exceeds $(+1/C)t$ or falls below $(-1/C)t$, wherein t is the time which has elapsed since the slope $+1/C$ was exceeded or $-1/C$ was fallen below. As long as the output state of the comparator 20 remains unchanged, the D-flipflop 21 similarly does not change state, so that the counter 25 is not reset by the exclusive OR gate 24. Consequently, the output value T of the counter 25, which is a measure for the time t, begins to increase. When the output value T of the counter 25 reaches the value $T_D$ which corresponds to a minimum chronological duration $t_D$, the comparator generates the detection signal DS which indicates that an event has been detected. The counter 25 continues count until it is reset to zero by the exclusive OR gate 24. This occurs when the amplitude of the depolarization signal IS exceeds $(-1/C)t$ or falls below $(+1/C)t$, since when this occurs the respective output states of the comparator 20 and the D-flipflop 21 will change. The overall chronological duration $t_T$ which has elapsed to this time since the slope $+1/C$ was exceeded or the slope $-1/C$ was fallen below corresponds to the output value $t_T$ of the counter 25. The value $t_T$ of the counter 25 is transferred into the register 27 and is transmitted therefrom into the memory 5. Transfer of the output value of the counter 25 into the register 27 before the counter 25 is reset to zero is achieved by the RS-flipflop 28 in combination with the AND gate 29. The RS-flipflop 28 is set by the occurrence of the signal DS from the comparator 26, so that a signal is supplied from the output Q of RS-flipflop 28 to one output of the AND gate 29. The other input of the AND gate 29 is connected to the output of the exclusive OR gate 24. When signals are present at both inputs of the AND gate 29, a pulse is supplied to the register 27 to effect the transfer.

The above procedure is repeated as soon as the slope of the depolarization signal IS again exceeds the value $+1/C$ or falls below the value $-1/C$.

The signal parameter which is used in the method and apparatus is thus the chronological duration for which the amplitude of the depolarization signal exceeds $(+1/C)t$ or falls below $(-1/C)t$. Measurement of this chronological duration t is begun at the time when the slope of the depolarization signal IS reaches the defined slope $+1/C$ or the slope $-1/C$. In order for a waveform within the depolarization signal IS to be detected as an event, the defined slope $+1/C$ must be exceeded or the defined slope $-1/C$ must be fallen below, and a defined minimum chronological duration $t_D$ must be reached during which the invent must exceed a defined amplitude $(+1/C)t$ or fall below a defined amplitude $(-1/C)t$.

The functioning of the circuit of FIG. 3, and the capability of that circuit to detect sequences of events indicating fibrillation of the heart, is further explained with reference to FIGS. 4 and 5.

Figure 4:
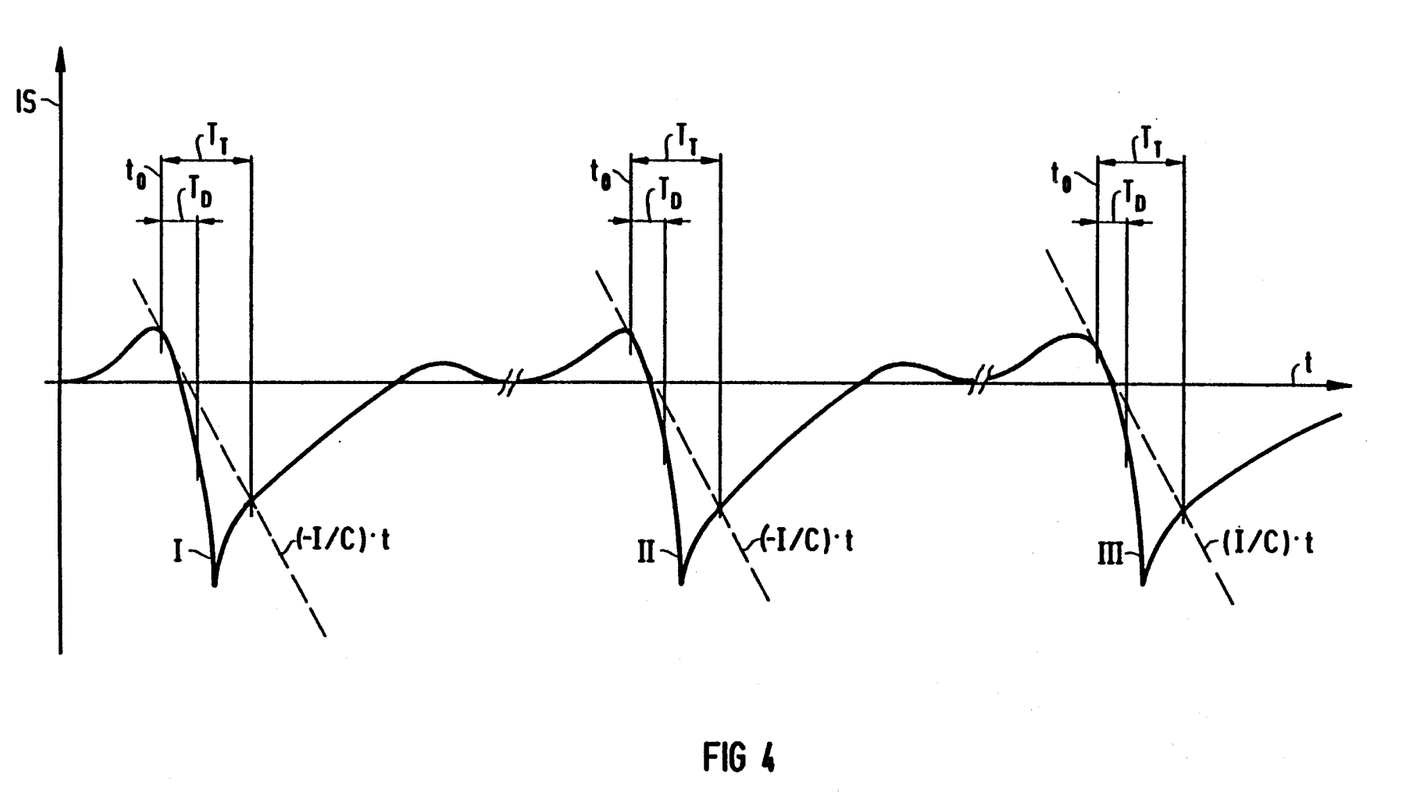
FIG. 4 shows a depolarization signal of a heart which contains a plurality of successive, normal events, for explaining the method and apparatus of the invention.

The depolarization signal of a heart functioning with a normal sinus rhythm is shown in FIG. 4. This is the signal which will exist at the output of the signal conditioning circuit 12 in the apparatus of FIG. 2. The illustrated portion of the depolarization signal contains three events, which are referenced I, II and III. Continually following the clock at the frequency $f_1$, the apparatus 1 checks whether the depolarization signal has a slope which exceeds the value $+1/C$ or falls below the value $-1/C$. (Although the depolarization signal is continuous, it may be considered as a succession of instantaneous valves, with each instantaneous value having a slope associated therewith) As long as this is not the case, the counter 25 is continually reset. In FIG. 4, the event I has a slope which falls below the value $-1/C$ for the first time, at time $t_O$. Beginning at this time, the counter 25 measures the chronological duration $t_T$ to that time at which the amplitude of the depolarization signal exceeds the value $(-1/C)t$. The path of the straight line $(-1/C)t$ is entered in FIG. 4, this straight line being tangent to the depolarization signal at time $t_O$, and intersecting the depolarization signal after the elapsation of the overall chronological duration $t_T$. Because, in the case of the event I, the overall chronological duration $t_T$ exceeds a minimum chronological duration $t_D$, for example 6 ms, the apparatus 1 generates a detection signal DS after the expiration of the minimum time $t_D$. Data corresponding to the overall chronological duration $t_T$ are transferred into the memory 5. The transferred data may correspond either to the overall chronological duration $t_T$ itself, or may correspond to the difference between the overall chronological duration $t_T$ and the minimum chronological duration $t_D$. It becomes clear from FIG. 4 that the standard deviation, calculated with respect to the transferred data for the most recently occurring events I-III, will fluctuate relatively slightly, because the overall chronological duration $t_T$ fluctuates only slightly for the individual event I through III.

Figure 5:
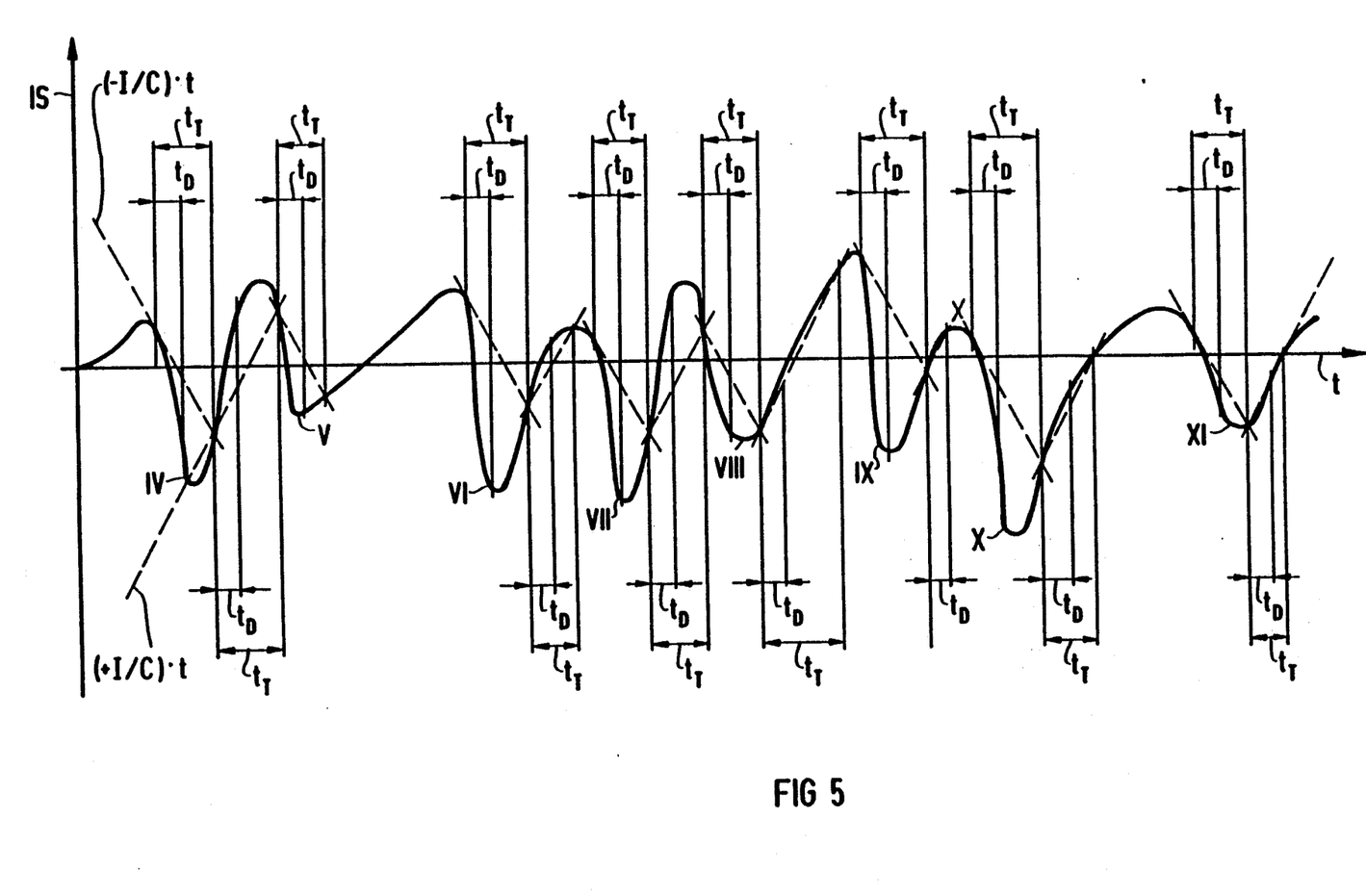
FIG. 5 shows a depolarization signal of a heart containing a sequence of abnormal events indicating fibrillation, for explaining the method and apparatus of the invention.

This is not true when fibrillation of the heart is present, and a depolarization signal for this condition is shown in FIG. 5. In this case, the overall chronological durations $t_T$, calculated for the individual events, fluctuate considerably. In contrast to FIG. 4 which shows the depolarization signal of a heart operating according to normal sinus rhythm, the leading edges of the events in the depolarization signal of FIG. 5, which is typical for fibrillation, are so steep that a detection is possible. This means that two detection signals DS are partially generated for the events IV-XI, because the minimum chronological duration is exceeded both in the case of the trailing edge and in the case of the leading edge of an event.

With reference to FIGS. 4 and 5, it is clear that the standard deviation S in the case of sinus rhythm is significantly less than in the case of fibrillation. Therefore, by comparing the standard deviation S to a suited rated value, one can determine whether a depolarization signal contains a sequence of events indicating fibrillation, or is composed entirely of such events. By additionally making reference to the heartbeat occurrence rate, as described in connection with FIG. 2, it is possible to unequivocally detect fibrillation of the heart.

The control logic 15 may be provided with a transmission/reception coil 30 connected to a terminal TM, as shown in FIG. 2, for the purpose of permitting bidirectional telemetric communication with an external device (not shown). Accordingly, there is the possibility of checking the data with respect to the signals DVA, DVS, and TV stored in the control logic 15, and to modify those signals as needed. The same possibility also exists with respect to the adjustability of the current sources 22, as well as with respect to the operational sine of the slope $1/C$.

The frequencies $f_1$ and $f_2$ are derived in a known manner from a crystal 31, also shown in FIG. 2 connected to the control logic 15 via a terminal C1.

Although modifications and changes may be suggested by those skilled in the art, it is the intention of the inventor to embody within the patent warranted hereon all changes and modifications as reasonably and properly come within the scope of this contribution to the art.

I claim as my invention:

1. A method for detecting a sequence of events indicating fibrillation among a plurality of normal events in the depolarization signal of a pathologically functioning heart, said method comprising the steps of:

acquiring the depolarization signa from the heart, said depolarization signal including a plurality of events, each event having a duration exceeding a minimum chronological duration and consisting of a plurality of successive instantaneous values, and said depolarization signal having a slope associated with each instantaneous value;

identifying, for each event a beginning time at which the absolute value of said slope of said depolarization signal exceeds the absolute value of a defined slope;

forming, for each event, a product of said defined slope and time elapsed since said beginning time;

measuring, for each event, the overall chronological duration for which the absolute value of said depolarization signal exceeds the absolute value of said product;

calculating a characteristic quantity corresponding to the statistical distribution of the overall chronological durations respectively measured for a most recently occurring event and a for a defined plurality of events appearing in succession immediately preceding said most recently occurring event; and comparing the calculated characteristic quantity to a defined rated value to obtain a comparison result identifying the presence of a sequence of events indicating fibrillation in said depolarization signal.

2. A method as claimed in claim 1 where the step of calculating a characteristic quantity corresponding to the statistical distribution of the overall chronological durations is further defined by the step of calculating the standard deviation of the overall chronological durations respectively measured for a most recently occurring event and for a defined plurality of events preparing in succession immediately preceding said most recently occurring event.

3. A method as claimed in claim 1 comprising the additional step of:

calculating, for each event, a difference value between the overall chronological duration for an event and said minimum chronological duration, and wherein the step of calculating a characteristic quantity corresponding to the statistical distribution of the overall chronological durations is further defined as the step of calculating a characteristic quantity corresponding to the statistical distribution of said difference values respectively calculated for a most-recently occurring event and for a defined plurality of events appearing in succession immediately preceding said most recently occurring event.

4. A method for detecting a sequence of events indicating fibrillation among a plurality of normal events in the depolarization signal of a pathologically functioning heart, said method comprising the steps of:
  acquiring the depolarization signal from the heart, said depolarization signal including a plurality of events, each event having a duration exceeding a minimum chronological duration and consisting of a plurality of successive instantaneous values, and said depolarization signal having a slope associated with each instantaneous value;
  identifying, for each event, a beginning time at which the absolute value of said slope of said depolarization signal exceeds the absolute value of a defined slope;
  forming, for each event, a product of said defined slope and time elapsed since said beginning time;
  measuring, for each event, the overall chronological duration for which the absolute value of said depolarization signal exceeds the absolute value of said product;
  calculating a characteristic quantity corresponding to the statistical distribution of the overall chronological durations respectively measured for a most recently occurring event and for a defined plurality of events appearing in succession immediately preceding said most recently occurring event;
  comparing the calculated characteristic quantity to a defined rated value to obtain a comparison result identifying the presence of a sequence of events indicating fibrillation in said depolarization signal;
  measuring the heartbeat occurrence rate of said heart;
  comparing the measured heartbeat occurrence rate to a defined limit value; and
  generating a signal indicating the presence of fibrillation in said depolarization signal when both said characteristic quantity exceeds said defined rated value and said heartbeat occurrence rate exceeds said defined limit value.

5. A method as claimed in claim 4 where the step of calculating a characteristic quantity corresponding to the statistical distribution of the overall chronological durations is further defined by the step of calculating the standard deviation of the overall chronological durations respectively measured for a most recently occurring event and for a defined plurality of events preparing in succession immediately preceding said most recently occurring event.

6. A method as claimed in claim 4 comprising the additional step of:
  calculating, for each event, a difference value between the overall chronological duration for an event and said minimum chronological duration,
and wherein the step of calculating a characteristic quantity corresponding to the statistical distribution of the overall chronological durations is further defined as the step of calculating a characteristic quantity corresponding to the statistical distribution of said difference values respectively calculated for a most recently occurring event and for a defined plurality of events appearing in succession immediately preceding said most recently occurring event.

7. An apparatus for detecting a sequence of events indicating fibrillation among a plurality of normal events in the depolarization signal of a pathologically functioning heart, comprising:
  means for acquiring the depolarization signal from the heart, said depolarization signal including a plurality of events, each event having a duration exceeding a minimum chronological duration and consisting of a plurality of successive instantaneous values, and said depolarization signal having a slope associated with each instantaneous value;
  means for identifying, for each event, a beginning time at which the absolute value of said slope of said depolarization signal exceeds the absolute value of a defined slope;
  means for forming, for each event, a product of said defined slope and time elapsed since said beginning time;
  means for measuring, for each event, the overall chronological duration for which the absolute value of said depolarization signal exceeds the absolute value of said product;
  means for calculating a characteristic quantity corresponding to the statistical distribution of the overall chronological durations respectively measured for a most recently occurring event and for a defined plurality of events appearing in succession immediately preceding said most recently occurring event; and
  means for comparing the calculated characteristic quantity to a defined rated value to obtain a comparison result identifying the presence of a sequence of events indicating fibrillation in said depolarization signal.

8. An apparatus as claimed in claim 7 wherein said means for calculating a characteristic quantity corresponding to the statistical distribution of the overall chronological durations is further defined as means for the step of calculating the standard deviation of the overall chronological durations respectively measured for a most recently occurring event and for a defined plurality of events preparing in succession immediately preceding said most recently occurring event.

9. An apparatus as claimed in claim 7 further comprising:
  means fir calculating, for each event, a difference value between the overall chronological duration for an event and said minimum chronological duration,
and wherein said means for calculating a characteristic quantity corresponding to the statistical distribution of the overall chronological durations is further defined as means for calculating a characteristic quantity corresponding to the statistical distribution of said difference values respectively calculated for a most recently occurring event and for a defined plurality of events appearing in succession immediately preceding said most recently occurring event.

10. An apparatus for detecting a sequence of events indicating fibrillation among a plurality of normal events in the depolarization signal of a pathologically functioning heart, comprising:
  means for acquiring the depolarization signal from the heart, said depolarization signal including a plurality of events, each event having a duration exceeding a minimum chronological duration and consisting of a plurality of successive instantaneous values, and said depolarization signal having a slope associated with each instantaneous value;
  means for identifying, for each event, a beginning time at which the absolute value of said slope of said depolarization signal exceeds the absolute value of a defined slope;

means for forming, for each event, a product of said defined slope and time elapsed since said beginning time;

means for measuring, for each event, the overall chronological duration for which the absolute value of said depolarization signal exceeds the absolute value of said product;

means for calculating a characteristic quantity corresponding to the statistical distribution of the overall chronological durations respectively measured for a most recently occurring event and for a defined plurality of events appearing in succession immediately preceding said most recently occurring event;

means for comparing the calculated characteristic quantity to a defined rated value to obtain a comparison result identifying the presence of a sequence of events indicating fibrillation in said depolarization signal;

means for measuring the heartbeat occurrence rate of said heart;

means for comparing the measured heartbeat occurrence rate to a defined limit value; and means for generating a signal indicating the presence of fibrillation in said depolarization signal when both said characteristic quantity exceeds said defined rated value and said heartbeat occurrence rate exceeds said defined limit value.

11. An apparatus as claimed in claim 10 wherein said means for calculating a characteristic quantity corresponding to the statistical distribution of the overall chronological durations is further defined as means for calculating the standard deviation of the overall chronological durations respectively measured for a most recently occurring event and for a defined plurality of events preparing in succession immediately preceding said most recently occurring event.

12. An apparatus as claimed in claim 10, further comprising:

means for calculating, for each event, a difference value between the overall chronological duration for an event and said minimum chronological duration, and wherein the said means for calculating a characteristic quantity corresponding to the statistical distribution of the overall chronological durations is further defined as means for calculating a characteristic quantity corresponding to the statistical distribution of said difference values respectively calculated for a most recently occurring event and for a defined plurality of events appearing in succession immediately preceding said most recently occurring event.

* * * * *

UNITED STATES PATENT AND TRADEMARK OFFICE
CERTIFICATE OF CORRECTION

PATENT NO : 6058599
DATED : May 9, 2000
INVENTOR(S) : Naoki Hanamura

It is certified that error appears in the above-identified patent and that said Letters Patent is hereby corrected as shown below:

Column 2, line 33, delete "th'se's," and insert --the--.

Column 4, line 9, delete "new" and insert --now--.

Column 5, line 14, delete "invent on" and insert --invention--.

Column 6, line 45, after "mounted", delete ". The" and insert --, the--.

Column 7, line 12, delete "it" and insert -- at--.

Column 7, line 28, delete "present" and insert --preset--.

Column 8, Claim 5, line 60, delete "are as" and insert --areas--; same line, delete "has" and insert --had--.

Column 8, Claim 5, line 61, delete "are as" and insert -- areas--.

Signed and Sealed this

Twenty-second Day of May, 2001

*Attest:*

NICHOLAS P. GODICI

*Attesting Officer*   Acting Director of the United States Patent and Trademark Office